United States Patent [19]

Haynes

[11] 4,067,883

[45] Jan. 10, 1978

[54] PROCESS FOR PREPARING A 4-HYDROXY-BENZODIOXOLE

[75] Inventor: Harold George Haynes, Royston, England

[73] Assignee: Fisons Limited, London, England

[21] Appl. No.: 621,213

[22] Filed: Oct. 9, 1975

Related U.S. Application Data

[63] Continuation of Ser. No. 249,899, May 3, 1972, abandoned.

[30] Foreign Application Priority Data

May 4, 1971 United Kingdom .............. 12870/71

[51] Int. Cl.$^2$ ........................................... C07D 317/44
[52] U.S. Cl. ..................... 260/340.5 R; 260/614 R; 260/615 A
[58] Field of Search ...................................... 260/340.5

[56] References Cited

U.S. PATENT DOCUMENTS

| 3,502,687 | 3/1970 | Biel ..................................... 260/293.4 |
| 3,736,338 | 5/1973 | Gates et al. ........................ 260/340.5 |

Primary Examiner—Ethel G. Love

Attorney, Agent, or Firm—Wenderoth, Lind & Ponack

[57] ABSTRACT

4-Hydroxy-benzodioxoles of formula

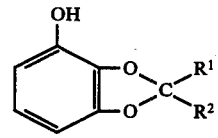

in which $R^1$ and $R^2$ are alkyl of 1 to 4 carbon atoms or together represent an alkylene chain of 5 to 7 carbon atoms, which can be converted to pesticides, e.g. by reaction with methyl isocyanate, are prepared by reacting pyrogallol with a ketal of formula

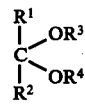

in which $R^3$ and $R^4$ are alkyl of 1 to 4 carbon atoms, at at least 90° C.

14 Claims, No Drawings

PROCESS FOR PREPARING A 4-HYDROXY-BENZODIOXOLE

This is a continuation of application Ser. No. 249,899, filed May 3, 1972, now abandoned.

The present invention relates to an improved process for preparing certain 4-hydroxy-benzodioxoles, compounds, prepared thereby and their use for the production of benzodioxolyl carbamates.

4-Benzodioxolyl carbonates of formula

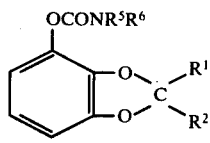

(I)

in which
R$^1$ and R$^2$ may be the same or different and each represents an alkyl group of 1 to 4 carbon atoms (e.g. methyl, ethyl or n-butyl) or together represent an alkylene chain of 5 to 7 carbon atoms (e.g. pentamethylene);
R$^5$ represents a hydrogen atom, an alkyl group of 1 to 4 carbon atoms (e.g. methyl or ethyl) or an alkanoyl group of 2 to 5 carbon atoms (e.g. acetyl or propionyl); and
R$^6$ represents an alkyl group of 1 to 4 carbon atoms (e.g. methyl or ethyl), an alkenyl group of 2 to 4 carbon atoms (e.g. allyl) or an alkynyl group of 2 to 4 carbon atoms (e.g. propargyl); are known as pesticides, particularly insecticides.

These pesticides can be made by reacting the corresponding 4-hydroxy-benzodioxole of formula

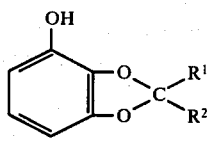

(II)

in which R$^1$ and R$^2$ are as defined above, with
a. an isocyanate of formula R$^6$NCO (R$^5$ in the product thus being hydrogen);
b. a carbamyl chloride of formula

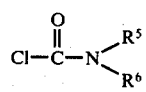

(except where R$^5$ is an alkanoyl group of 2 to 5 carbon atoms);
c. phosgene to form the corresponding 1,3-benzodioxolyl-4-chloroformate and reacting this with an amine or amide of formula

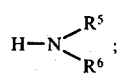

or
d. where R$^5$ is an alkanoyl group of 2 to 5 carbon atoms, acylating the corresponding compound in which R$^5$ is hydrogen, prepared by process (a), (b) or (c).

The 4-hydroxy-benzodioxoles of formula (II) can be made by reacting pyrogallol, which has the formula

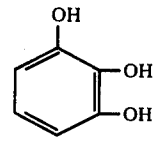

with a ketone of the formula

in which R$^1$ and R$^2$ are as defined above.

An improved process of the production of the 4-hydroxybenzodioxoles of formula II has now been discovered, in which they are produced in surprisingly high yield under surprising reaction conditions.

The invention provides a process for preparing a 4-hydroxybenzodioxole of the formula

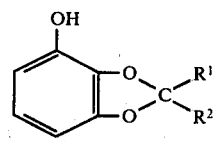

(II)

in which R$^1$ and R$^2$ are the same or different and each represents an alkyl group of 1 to 4 carbon atoms or together represent an alkylene chain of 5 to 7 carbon atoms, which process comprises reacting pyrogallol with a ketal of the formula

(III)

in which R$^1$ and R$^2$ are as defined above and R$^3$ and R$^4$ are the same or different and each represents an alkyl group of 1 to 4 carbon atoms (e.g. methyl, ethyl, normal propyl, isopropyl, normal butyl or secondary butyl) at at least 90° C. Such a reaction temperature is particularly surprising since the prior art would teach one to use a significantly lower temperature for the present ketal exchange reaction

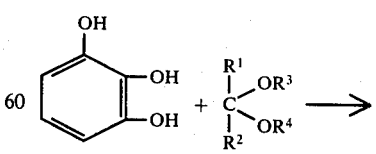

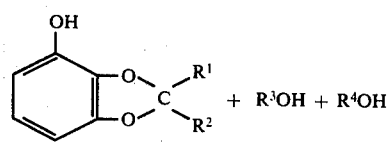

Furthermore, the prior art would teach one to carry out this reaction in the presence of such acids as p-toluene sulphonic acid, ammonium chloride or Amberlite IR 120 H+ sulphonic acid ion exchange resin as catalysts. It can be seen that these prior art catalysts not only include acids themselves but also include materials which provide acid under the reaction conditions. Contrary to this teaching of the prior art, it has been discovered that these materials in fact mar the present reaction, decreasing the yield. Thus, the present reaction is preferably carried out in the presence of much less acid than taught by the prior art, especially in the complete absence of acid. The reaction is desirably conducted in the presence of less than 0.00005 g mols, preferably less than 0.00001 g mol, of acid per g mol of pyrogallol employed, and especially in the complete absence of acid.

The reaction is desirably conducted in the presence of less than 0.00005 g mols, preferably less than 0.00001 g mol, in toto per g mol of pyrogallol employed, of any material which is not pyrogallol, a ketal of formula III, a reaction product or an inert diluent. Especially preferred in carrying out the reaction in the complete absence of such material Usually $R^3$ and $R^4$ are the same. Preferably they represent methyl groups. $R^1$ and $R^2$ are also usually the same as each other, and preferably both represent methyl groups.

The reaction is preferably carried out at least 100° C, especially at 100° to 150° C, in particular 110° to 145° C.

The reaction is preferably continued until substantially no pyrogallol remains.

Usually, the reaction is carried out in the presence of an inert solvent for the reaction, preferably such a solvent having a boiling point in the range 90° – 150° C. Suitable as solvent is toluene, xylene or tetrachloroethylene, especially toluene and most preferably xylene. The solvent may be a mixture of compounds.

Preferably, the reaction is carried out while distilling solvent and by-product alkanol from the reaction mixture. Fractionation during the reaction is not essential when using xylene as solvent, nonfractional distillation being adequate.

The time during which the mixture of pyrogallol, ketal and solvent is above about 80° C without distillation should be short to minimise side reactions. Having heated a mixture of them as far as 80° C, therefore, it is desirable to start distillation as soon as possible, e.g. within ¼ hour.

Conveniently the solvent is chosen so that on distillation of the reaction mixture, the boiling point is the desired reaction temperature Solvent thus distils off during the distillation and accordingly more solvent can be added to the reaction mixture, if necessary, to maintain the desired temperature and to prevent the bulk of the reaction mixture becoming too small, when the tendency for side reactions is increased.

Preferably, throughout the present reaction the reaction mixture weighs at least 400 g, especially at least 500 g, per g mol of pyrogallol employed.

If some of the ketal of formula III distils over, and hence reactant is removed, as usually happens for example when the comparatively low boiling 2,2-dimethoxypropane is the ketal, then more of the ketal may be added to the reaction medium during the distillation.

In the most preferred embodiment, the 4-hydroxy-benzodioxole of formula II is 2,2-dimethyl-4-hydroxy-1,3-benzodioxole. This can be made by reaction of pyrogallol and 2,2-dimethoxypropane:

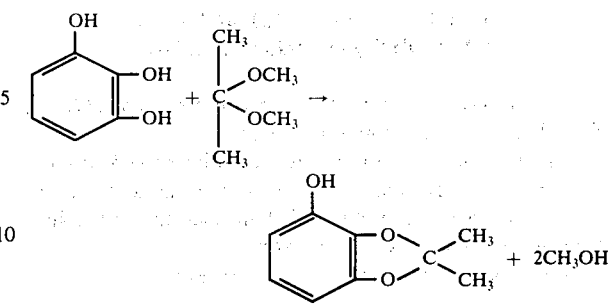

A preferred embodiment is thus a process for preparing 2,2-dimethyl-4-hydroxy-1,3-benzodioxole which comprises reacting pyrogallol with 2,2-dimethoxypropane at at least 90° C and in the presence of an inert solvent for the reactant and in the complete absence of any material which is not pyrogallol, 2,2-dimethoxypropane, a reaction product or an inert diluent, the weight of reaction mixture being preferably at least 400 g per mole of pyrogallol employed, while distilling off solvent and methanol from the reaction mixture and adding to the reaction mixture more 2,2-dimethoxypropane and, if necessary, to maintain the reaction temperature and preferably to maintain the weight of reaction mixture throughout the reaction at at least 400 g per mole of pyrogallol employed, more solvent, during the distillation. The reaction is preferably carried out by mixing pyrogallol with 2,2-dimethoxypropane (e.g. 1 g mol/g mol of pyrogallol), adding a solvent, e.g. xylene, in amount to make up a minimum weight of reaction medium of 500 g per g mol of pyrogallol employed, and distilling the mixture whilst adding 2,2-dimethoxypropane and, if necessary, more solvent, to maintain the reaction temperature and a minimum weight of reaction medium of 500 g per g mol of pyrogallol employed, until substantially no pyrogallol remains. The reaction may take about 3–12 hours.

When $R^2$ (or $R^1$) represents a primary or secondary alkyl group of 1 to 4 carbon atoms, there may be produced in the present process unsaturated by-product derived by the elimination of a molecule of alkanol $R^4OH$ (or $R^3OH$) from the ketal of formula III, e.g.

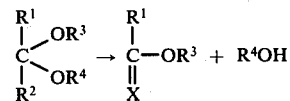

where $R^1$, $R^3$ and $R^4$ are as defined above and XH equals $R^2$. Thus, when the ketal of formula III is 2,2-dimethoxypropane, 2-methoxypropene may be produced and may be found in the distillate when distillation of the reaction mixture is employed.

The unsaturated compound may be recombined with alkanol $R^4OH$ (or $R^3OH$) in the reverse of the reaction shown in the equation immediately above in the presence of a catalyst which is a strong cation exchange resin in the acid form, e.g. a sulphonic acid ion exchange resin in the acid form. The ion exchange resin must be sufficiently strongly acid to catalyse the reaction, e.g. as strong as the sulphonic acid ion exchange resins. Suitable ion exchange resins in the acid form are the sulphonic acid cross linked polystyrene ion exchange resins in the acid form. Specific examples of suitable resins are the acid form of Amberlite IR 120 or Zeo-Karb 325.

Since water may have an adverse affect on the dialkoxy product, it may in some instances be desirable to dry the resin, e.g. at 110° C for an hour. In view of the small resin: liquid ratio normally used, however, even large percentages of water in the resin generally have but little effect. The recombination is of particular interest where the alkanol is a normal alkanol. Preferably $R^4$ represents a methyl or ethyl group. Thus, for example 2-methoxypropene and methanol may be combined:

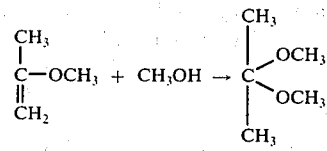

In the present process where $R^2$ represents a primary or secondary alkyl group of 1 to 4 carbon atoms, therefore, it is advantageous to admix any of the unsaturated by-product as described and alkanol with the ion exchange resin in acid form and hence to produce ketal of formula III, and preferably then to recycle this ketal produced for reaction with pyrogallol according to the ketal exchange process. This recycling is desirably done after removal of the resin (e.g. by filtration or decanting or by employing a column of the resin down which the reactants are passed) and preferably also after any excess alkanol $R^3OH$ or $R^4OH$ has been removed, e.g. by extraction with a neutral salt solution such as saturated calcium chloride solution or preferably saturated sodium solution, or less preferably by aqueous caustic soda extraction and then fractionating.

The recombination of unsaturated compound with alkanol is conveniently conducted in the solvent in which the ketal exchange process occurred, and is suitably conducted in the range 10°-60° C. Preferably the essential materials are brought into contact with one another at ambient temperature. As the reaction is exothermic, cooling may be desirable if the amount of the unsaturated compound is large. Preferably the mol ratio of alkanol to unsaturated compound is at least 1:1. Usually, the amount of catalyst is at least 0.1%, preferably at least 0.6%, by weight of the unsaturated compound. For reasons of economy, the amount of catalyst (calculated in the dried state) is usually no more than 12% by weight of unsaturated compound.

A preferred group of pesticides of formula I are those where $R^5$ represents a hydrogen atom. Such compounds can be made by reaction of the 4-hydroxy-benzodioxole of formula II with an isocyanate of formula $R^6NCO$ where $R^6$ is as defined above. The reaction is usually carried out at a temperature from 0° to 150° C, for example at ambient temperature, at a pressure of 0.5-10 atmospheres, preferably at 1-1.1 atmospheres, in an organic solvent, e.g. acetone or a hydrocarbon (e.g. toluene), and preferably also in the presence of a catalyst (usually a tertiary amine, e.g. triethylamine or pyridine, or an organotin compound, e.g. dibutyltin diacetate). Where $R^6$ is methyl, as is preferred, the reaction is usually carried out in a vessel at 1-1.1 atmospheres and at a temperature within the range 0° to 60° C because of the boiling point of methyl isocyanate. Advantageously, the 4-hydroxy-benzodioxole product of the ketal exchange process is reacted with the isocyanate without isolation. Thus a solution of it produced in the ketal exchange process can be reacted as such with isocyanate.

The pesticides of formula I except where $R^5$ is an alkanoyl group of 2 to 5 carbon atoms may also be prepared by reaction of the 4-hydroxy-benzodioxole of formula II with a carbamyl chloride of formula

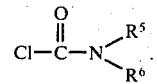

The reaction is usually carried out from 0° to 150° C, preferably with an equimolar amount of inorganic or tertiary organic base and preferably also in an inert solvent.

The pesticides of formula I may also be prepared by (i) reaction of the 4-hydroxy-benzodioxole of formula II with phosgene to form the corresponding 1,3-benzodioxolyl-4-chloroformate, and (ii) reacting this with an amine of formula

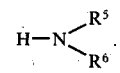

Reaction (i) is usually carried out from 0° to 150° C, preferably in a hydrocarbon solvent and preferably also in the presence of an equimolar amount of a weak tertiary base (e.g. dimethylaniline). Reaction (ii) is usually carried out from 0° to 150° C with or without an inert solvent (e.g. hydrocarbon or ether) and preferably in the presence of an equimolar amount of an inorganic base (e.g. sodium carbonate) or organic base (which may be an excess of the reacting amine or may for example be a tertiary amine such as triethylamine).

The pesticides of formula I where $R^5$ is an alkanoyl group of 2 to 5 carbon atoms may be prepared by acylating the corresponding compound in which $R^5$ is hydrogen which can be prepared as described above. The acylation is carried out by reaction with acylating agent, e.g. of formula $(R^5CO)_2O$ or $R^5COX$ where X is halogen, usually chlorine. The reaction is usually carried out from 0° to 150° C with or without an inert solvent. When the acylating agent is an acid anhydride, the reaction is preferably carried out in the presence of an acylation catalyst, e.g. concentrated sulphuric acid.

Preferred pesticides of formula I are those where $R^6$ represents an alkyl group of 1 to 4 carbon atoms, particularly methyl. Preferably also $R^5$ represents a hydrogen atom. Especially preferred is the pesticide 2,2-dimethyl-1,3-benzodioxol-4-yl N-methylcarbamate.

The invention is illustrated by the following Examples, in which percentages are by weight unless otherwise indicated.

EXAMPLE 1

126 gms. (1 g mol) of pyrogallol was dissolved in 208 gms (2 g mols) of hot 2,2-dimethoxypropane, and toluene (875 mls) was added. Then, whilst distilling for 10 hours, maintaining the temperature of the reaction mixture of 110° C, 1,925 mls of distillate was collected and a further 9.2 g mols of 2,2-dimethoxypropane and 525 mls toluene were added to the reaction mixture. Negligible pyrogallol remained and the residue weighed 650 g and contained by GLC (gas liquid chromatographic) analysis, 142 gms., equivalent to 86% yield from pyrogallol, of 2,2-dimethyl-4-hydroxy-1,3-benzodioxole.

EXAMPLE 2

Example 1 was carried out but to the residue, which was a solution of the desired product, were added at ambient temperature 1.12 g mols of methyl isocyanate together with 0.05 g triethylamine. After 4 hours, there was obtained, according to infra red analysis, a total of 178 g., representing 80% yield from pyrogallol, of 2,2-dimethyl-1,3-benzodioxol -4-yl N-methylcarbamate, of which 156 g was readily precipitated in the form of approximately 98% pure solid from the toluene solution.

EXAMPLE 3

Example 1 was carried out. The distillate from the ketal exchange reaction containing some 2-methoxypropene as well as methanol, 2,2-dimethoxypropane and toluene. The 2-methoxypropene was recombined with equivalent methanol by the addition as catalyst of 2% weight/volume dried acid form Amberlite 120 sulphonic acid ion exchange resin with esternal water cooling. The distillate was then found to contain, by GLC analysis, 9.32 g mols of 2,2-dimethoxy-propane, so that the nett usage was 1.88 g mols., and the yield of 2,2-dimethyl-4-hydroxy -1,3-benzodioxole from nett 2,2-dimethoxy-propane was 50%. The distillate, after decanting from the resin and removing methanol by aqueous alkali extraction and then fractionating, could then be recycled to the ketal exchange stage.

EXAMPLE 4

1 g mol of pyrogallol was mixed with 1 g mol of hot 2,2-dimethoxy propane, and 875 mls of toluene were added. Then, whilst distilling for 6 hours, maintaining the temperature of the reaction mixture at 115° C., 875 mls of distallate was collected and a further 3 g mols of 2,2-dimethoxypropane and 75 mls of toluene were added to the reaction mixture. Negligible pyrogallol remained and the residue weighed 520 g and contained, by GLC analysis, 144 gms., equivalent to 86% yield, of the desired product 2,2-dimethyl-4-hydroxy-1,3-benzodioxole.

EXAMPLES 5 and 6

The process was as in Example 4 but with the following variations —

|  | Example 5 | Example 6 |
| --- | --- | --- |
| Solvent | Xylene, mixed isomers | Tetrachloroethylene |
| Mls solvent added initially | 750 | 750 |
| Mls solvent added during reaction | None | None |
| Reaction time | 6 hrs | 12 hrs |
| Reaction temperature | about 125° C | 115° C |
| 2,2-dimethoxypropane added during the reaction period, g mols | 6 | 17 |
| Distillate volume, mls | 580 | 2,170 |
| Yield, % from pyrogallol, by GLC | 85 | 79 |
| Reaction residue weight, g | 650 | 1,270 |

EXAMPLE 7 a. 1 g mol (126 g) of pyrogallol (containing less than 0.3% water) was dissolved by heating in a mixture of 1.5 g mols (156 g., 185 mls) of 2,2-dimethoxypropane and 480 mls of toluene. The mixture was distilled at the rate of 140 mls per hour, adding toluene at the same rate, until the reaction mixture reached 115° C. This took about 1½ hours. Then, 2½ g mols of 2,2-dimethoxypropane were pumped in, below the liquid level, over a period of 4¼ - 4½ hours, allowing the reaction temperature to rise to 120° C, while continuing distillation at 140 mls per hour and adding toluene if necessary to obtain 400 g of reaction mixture at the end of the distillation. Distillation was continued until the vapour temperature was at least 102° C (indicating that negligible 2,2-dimethoxy propane remained in the reaction mixture) and analysis revealed that not more than 2% of the initial pyrogallol remained unreacted.

b. The residue weighed 400 g and contained about 38% by weight 2,2-dimethyl-4-hydroxy-1,3-benzodioxole. The residue was cooled to 25°–30° C and a trace, e.g. ¼ ml, of triethylamine was added. Then, in two lots, with cooling between, 1.12 g mols of methyl isocyanate were added. Precipitation was permitted at 15°–25° C for at least 4 hours.

c. While rigidly excluding water, material boiling below toluene, and in particular excess methyl isocyanate, was fractioned off (and recycled to the methyl isocyanate addition stage). While still rigidly excluding water, toluene was then distilled off, and then fractionated off under reduced pressure. (The distillate was re-fractionated and the pure toluene fraction recycled to the ketal exchange stage.) The residue was then dried, to give a 91% yield of 2,2-dimethyl-1,3-benzodioxol-4-yl N-methylcarbamate, based on the initial pyrogallol.

EXAMPLE 8

Example 7 was carried out up to but excluding stage (c).

c. The precipitate was filtered off at a temperature not exceeding 21° C and washed with a little toluene. A 77% yield of 2,2-dimethyl-1,3-benzodioxol-4-yl N-methylcarbamate was thus obtained, based on the initial pyrogallol.

d. From the filtrate and washings, while rigidly excluding water, any material, and in particular methyl isocyanate, boiling below toluene was fractionated off for recycling to the methyl isocyanate addition stage (b). Then, while rigidly excluding water, most of the toluene was distilled off. While still rigidly excluding water, most of the remaining toluene was then fractionated off under reduced pressure. (The distillate was re-fractionated and the pure toluene fraction recycled to the ketal exchange stage (a).) Finally, still rigidly excluding water, 2,2-dimethyl-1,3-benzodioxol-4-yl N-methylcarbamate (vapour temperature 127°–140° C) was distilled off at 3 mms. pressure until a maximum residue temperature of 200° C had been reached. A 12% yield of the compound, based on initial pyrogallol, was thus obtained, making a yield of 89% in all of the compound in this Example, based on initial pyrogallol.

EXAMPLE 9

Example 8 was carried out, and in addition the distillate from stage (a) was agitated, under a reflux condenser, with 0.2% weight/volume of dried acid from Amberlite 120 sulphoic acid ion exchange resin. The mixture was then cooled to not more than 25° C and decanted off from the ion exchange resin. Methanol (and part of any acetone) were then removed by one extraction with an equal volume of 16% by weight NaOH in water.

The aqueous extract was boiled to remove solvents and the residue was recycled after adding water to adjust to 16% by weight NaOH.

The organic layer from the extraction stage was dried by extracting with ¼ the volume of 48% by weight NaOH in water, and then fractionated and the fractions containing pure 2,2-dimethoxypropane and/or toluene recycled to the ketal exchange stage (a).

EXAMPLE 10 a. 1 g mol (126 g) of pure grade pyrogallol (containing less than 0.3% water) was dissolved by heating with agitation in 1.125 g mols (117 g, 138 mls) of 2,2-dimethoxypropane and 525 mls of toluene. The resulting mixture was distilled at the rate of 140 mls per hour, adding toluene at the same rate, until the reaction mixture reached 115° C. This took about 1½ hours. Then, 1.875 g mols (195 g, 231 mls) of 2,2-dimethoxypropane were pumped in below the liquid level, over a period of 4¼ - 4½ hours, allowing the temperature to rise to 120° C, while distilling at 110 mls per hour. The weight of the reaction mixture was not allowed to fall below 450 g., toluene being added to maintain this minimum weight. After all the 2,2-dimethoxypropane had been added, distillation was continued until the vapour temperature was at least 102° C (indicating that negligible 2,2-dimethoxypropane remained in the reaction mixture). Analysis revealed that not more than 2% of the initial pyrogallol remained unreacted.

b. The residue weighed 500 g. It was cooled to 22°-30° C and a trace, e.g. ¼ ml, of triethylamine was added. Then, in two lots, with cooling between, 1.15 g mols of methyl isocyanate were added. precipitation was permitted for at least 4 hours.

While rigidly excluding water, most of the excess methyl isocyanate was distilled off (until a vapour temperature of 80° C had been reached) and this was recycled to the methyl isocyanate addition stage. The residue was then cooled to 15°-22° C with stirring. Reprecipitation occurred. The precipitate was filtered off, washed with a little toluene and dried at less than 60° C. An 82% yield of 2,2-dimethyl-1,3-benzodioxol-4-yl N-methylcarbamate, based on the initial pyrogallol, was thus obtained. Toluene was recovered from the filtrate as in Example 8 and recycled to stage (a).

EXAMPLE 11

Example 10 was carried out, and in addition the distillate from stage (a), after standing for less than a day, was agitated, under a reflux condenser, with 0.2% weight/volume of dried (at 105° C) acid form Amberlite 120 sulphonic acid ion exchange resin. The mixture was then cooled to not more than 25° C and decanted off from the ion exchange resin. Methanol and part of any acetone were removed by one extraction with an equal volume of 16% by weight NaOH in water.

The aqueous extract was boiled to a vapour temperature of 100° C to remove solvents and the residue was recycled after adding water to adjust to 16% by weight NaOH.

The organic layer from the extraction stage was dried by extracting with ¼ the volume of 48% by weight NaOH in water, and then fractionated and the fractions containing pure 2,2-dimethoxypropane and/or toluene recycled to the ketal exchange stage.

EXAMPLE 12

Example 11 was repeated but using 0.4% weight/volume of acid form Amberlite 120 sulphonic acid ion exchange resin containing 50% by weight of water, in place of the 0.2% weight/volume dried ion exchange resin. The yield of 2,2-dimethoxypropane was unaffected.

EXAMPLE 13 a. 1 g mol (126 g) of pure grade pyrogallol was mixed with 1,125 g mols (117 g., 138 mls) of 2,2-dimethoxypropane and 525 mls of xylene (mixed isomers). The mixture was heated to boiling over 20 minutes, then distilled at 130 mls/hr, (i) for 1 hour, adding xylene at the same rate and then (ii) for 4 hours, meanwhile adding 95 mls of xylene and pumping in below the liquid level 1.64 g mols of 2,2-dimethoxypropane. The residue (500 g) was distilled down to 413 g and found to contain, by analysis, negligible pyrogallol and 152 g., equivalent to a 92% yield, of 2,2-dimethyl-4-hydroxy-1,3-benzodioxole.

b. The residue was cooled to 45° C., a trace (½ ml) of triethylamine added, then in two lots, with cooling between, 1.1 g mols of methyl isocyanate. After 4 hours agitation at 20°-25° C., isopropylamine (4 mls) was added to destroy the unreacted methyl isocyanate. After agitating for 1 hour further, the precipitate was filtered off, washed with 100 ml of xylene and dried giving 192 g, representing an 86% yield, of 2,2-dimethyl-1,3-benzodioxol-4-yl N-methylcarbamate.

EXAMPLE 14

Example 13 was carried out, and in addition the following stages:

c. The distillate from stage (a) was agitated for ½ hour under a reflux condenser with 0.2% weight/volume Amberlite 120 sulphonic acid ion exchange resin, cooled to 25° C. and the resin removed. After 2 extractions at 26° C with an equal volume of aqueous sodium sulphate saturated at 20.5° C, then drying over sodium sulphate, the xylene solution contained, by analysis, 144 g of 2,2-dimethoxy-propane and was suitable for recycling to stage (a).

d. The filtrate from stage (b) was agitated with one third its volume of 5N aqueous sodium hydroxide solution for 1 hour at 20°-30° C. The aqueous layer was separated off and contained 10 g of 2,2-dimethyl-4-hydroxy-1,3-benzodioxole. The xylene layer was washed with 3N sulphuric acid, then washed with water until neutral, then fractionated. The fraction of boiling point 138°-142° C (216 mls) was xylene suitable for recycling to stage (c).

EXAMPLE 15

Part (a) of the process described in Example 13 was repeated using, in place of 2,2-dimethoxypropane, equivalent 2,2-diethoxypropane. The yield of 2,2-dimethyl-4-hydroxy-1,3-benzodioxole from pyrogallol was 91%.

I claim:

1. Process for preparing a 4-hydroxy-benzodioxole of the formula

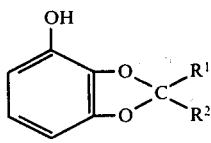

(II)

in which $R^1$ and $R^2$ are the same or different and each represents alkyl of 1 to 4 carbon atoms or together represent alkylene of 5 to 7 carbon atoms, which process comprises the step of reacting pyrogallol with a ketal of the formula

(III)

in which $R^1$ and $R^2$ are as defined above and $R^3$ and $R^4$ are the same or different and each represents alkyl of 1 to 4 carbon atoms, at a temperature of at least 90° C in the absence of any material which is not pyrogallol, the ketal, a reaction product of the process claimed herein or an inert diluent.

2. process according to claim 1 wherein the reaction is carried out at a temperature of at least 100° C.

3. Process according to claim 1 wherein the reaction is carried out at 100°–150° C.

4. Process according to claim 1 wherein $R^3$ and $R^4$ are the same.

5. Process according to claim 4 wherein $R^3$ and $R^4$ each represent methyl or ethyl.

6. Process according to claim 1 wherein $R^1$ and $R^2$ each represent methyl.

7. Process according to claim 1 wherein the reaction is carried out in the presence of an inert solvent for the reactants, the solvent having a boiling point in the range 90° to 150° C.

8. Process according to claim 1 wherein the reaction is carried out in the presence of an inert solvent selected from the group consisting of toluene, xylene and tetrachloroethylene.

9. Process according to claim 1 wherein the reaction is carried out in the presence of an inert solvent for the reactants and while distilling solvent and product $R^3OH$ from the reaction mixture.

10. Process according to claim 9 wherein more solvent is added to the reaction mixture during the distillation.

11. Process according to claim 9 wherein more ketal of formula III is added to the reaction mixture during the distillation.

12. Process according to claim 1 wherein throughout the reaction the reaction mixture weighs at least 400 g per g mol of pyrogallol employed.

13. Process for preparing 2,2-dimethyl-4-hydroxybenzodioxole which comprises the step of reacting pyrogallol with 2,2-dimethoxypropane at a temperature of at least 90° C in the presence of an inert solvent for the reactants and in the absence of any material which is not pyrogallol, 2,2-dimethoxypropane, a reaction product or an inert diluent, while distilling off the solvent and methanol from the reaction mixture and adding to the reaction mixture additional 2,2-dimethoxypropane during the distillation.

14. Process according to claim 13 wherein additional solvent is added to the reaction mixture during the distillation to maintain the reaction temperature.

* * * * *